(12) United States Patent
Izmailov et al.

(10) Patent No.: US 7,386,399 B1
(45) Date of Patent: Jun. 10, 2008

(54) METHOD AND APPARATUS FOR ALIGNMENT OF DNA SEQUENCING DATA TRACES

(75) Inventors: Alexandre M. Izmailov, Etobicoke (CA); Thomas D. Yager, Mississauga (CA)

(73) Assignee: Siemens Healthcare Diagnostics Inc.

( * ) Notice: Subject to any disclaimer, the term of this patent is extended or adjusted under 35 U.S.C. 154(b) by 685 days.

(21) Appl. No.: 09/827,432

(22) Filed: Apr. 6, 2001

Related U.S. Application Data

(63) Continuation-in-part of application No. 09/628,736, filed on Jul. 27, 2000, now Pat. No. 6,397,150.

(51) Int. Cl.
*G01N 33/48* (2006.01)
(52) U.S. Cl. ...................................... 702/20
(58) Field of Classification Search ............... 702/20; 435/91.2, 6
See application file for complete search history.

(56) References Cited

U.S. PATENT DOCUMENTS

| | | | |
|---|---|---|---|
| 4,849,513 A | 7/1989 | Smith et al. |
| 4,855,225 A | 8/1989 | Fung et al. |
| 5,118,800 A | 6/1992 | Smith et al. |
| 5,124,247 A | 6/1992 | Ansorge |
| 5,171,534 A | 12/1992 | Smith et al. |
| 5,213,673 A | 5/1993 | Fujimiya et al. |
| 5,268,486 A | 12/1993 | Waggoner et al. |
| 5,365,455 A | 11/1994 | Tibbetts et al. |
| 5,608,063 A | 3/1997 | Hobbs, Jr. et al. |
| 5,614,386 A | 3/1997 | Metzker et al. |
| 5,666,435 A | 9/1997 | Burgi et al. |
| 5,710,628 A | 1/1998 | Waterhouse et al. |
| 5,751,534 A | 5/1998 | DeBalko |
| 5,789,168 A | 8/1998 | Leushner et al. |
| 5,821,058 A | 10/1998 | Smith et al. |

(Continued)

FOREIGN PATENT DOCUMENTS

WO     WO 95 11961     5/1995

(Continued)

OTHER PUBLICATIONS

Giddings et al., Genome Research, vol. 8, pp. 644-665, 1998.*

(Continued)

*Primary Examiner*—Cheyne D Ly
(74) *Attorney, Agent, or Firm*—Christopher L. Wight; Brinks Hofer Gilson & Lione

(57) ABSTRACT

The present invention is directed to a method for alignment of nucleic acid data traces. The method involves selecting reference alignment points from among internal peaks representing highly conserved bases, preferably consisting of heterogeneous multiplets. The alignment points may also optionally include the primer peak and/or the full-length peak. Reference position numbers are assigned to these alignment points reflecting the known relative position of the alignment point, a sequence position number is assigned to peaks in the data traces so as to maximize assigning the sequence position number and the reference position number to the same base. Optionally, the method may include the step of determining the average peak spacing interval between alignment points and assigning a sequence position number to peaks occurring at the intervals. The data traces are then aligned based on the assigned sequence position numbers.

13 Claims, 14 Drawing Sheets

Deviation of the Peak Position (in Number of Bases) from the Average as a Function of Base Number in the Traces Aligned with Internal Standards (long gel, M13, 17 peaks, 5-th degree polynomial)

U.S. PATENT DOCUMENTS

| | | | |
|---|---|---|---|
| 5,830,657 | A | 11/1998 | Leushner et al. |
| 5,834,189 | A | 11/1998 | Stevens et al. |
| 5,916,747 | A | 6/1999 | Gilchrist et al. |
| 5,981,186 | A | 11/1999 | Gabe et al. |
| 6,005,663 | A | 12/1999 | Waterhouse et al. |
| 6,027,709 | A | 2/2000 | Little et al. |
| 6,068,737 | A | 5/2000 | De Chamorro et al. |

FOREIGN PATENT DOCUMENTS

| | | | |
|---|---|---|---|
| WO | WO 97 40184 | | 10/1997 |
| WO | WO 98/00708 | * | 1/1998 |
| WO | WO 98 41650 | | 9/1998 |
| WO | WO 00 68410 | | 11/2000 |

OTHER PUBLICATIONS

Ewing et al., Genome Research, vol. 8, pp. 175-185, 1998.*

Allex et al., Proceedings of the Fourth International Conference on Intelligent Systems for Molecular Biology, St.. Louis, MO, AAAI, pp. 3-14, 1996.*

Allex et al., Proceedings of the Fifth International Conference on Intelligent Systems for Molecular Biology, Halkidiki, Greece, AAAI, pp. 1-12, 1997.*

Yager et al., Electrophoresis, 1999, vol. 20, 1280-1300, May 1999.*

Michael C. Giddings, et al., An adaptive, object oriented strategy for base calling in DNA sequence analysis Nucleic Acids Reseacrch, 1993, vol. 21, No. 19.

James B. Golden, III, et al., Pattern Recognition for Automated DNA Sequencing: I. On-line Signal Conditioning and Feature Extraction for Basecalling: Dept. of Mechanical Engineering, Dept. of Microbiology and Immunology, Vanderbilt University Schools of Medicine and Engineering, Nashville, TN 37232-2363. Proc Int Conf. Intell: Syst Mol Biol 1993; 1, 136-44.

Lance B. Koutny, et al., Automated Image Analysis for Distortion Compensation in Sequencing Gel Electrophoresis: 1369 Applied Spectroscopy 46(1992 Jan. No. 1, Frederick, MD. US.

Keith Kretz, et al., Cycle Sequencing, PCR Methods and Applications S107-S112., Manual Supplement PCR Methods Appl. 1994 vol. 3.

Michael A. Reeve et al., A novel thermostable polymerase for DNA sequencing; Nature, vol. 376, Aug. 31, 1995.

Gualberto Ruano, et al., Coupled amplification and sequencing of genomich DNA: Proc. Natl. Acad. Sci. USA, vol. 88, pp. 2815-281, Apr. 1991. Genetics.

Stefan Wiemann, et al., Simultaneous On-Line DNA Sequencing on Both Strands with Two Fluorescent Dyes: Analytical Biochemistry 224, 117-121 (1995).

Tibbetts, C., Bowling, J.M., and Golden, J.B. (1993). Neural Networks for Automated Basecalling of Gel-based DNA Sequencing Ladders, in Venter, J.C., and Adams, M., eds., *Automated DNA Sequencign and Analysis Techniques*, Academic Press, 219-229.

* cited by examiner

SEQUENCE LISTING

<160> NUMBER OF SEQ ID NOS: 5

<210> SEQ ID NO 1
<211> LENGTH: 12
<212> TYPE: DNA
<213> ORGANISM: Human immunodeficiency virus

<400> SEQUENCE: 1
gaaaaaataa ag                                                          12

<210> SEQ ID NO 2
<211> LENGTH: 23
<212> TYPE: DNA
<213> ORGANISM: Human immunodeficiency virus
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 2
tggccnttna cagaagaaaa nat                                              23

```
<210> SEQ ID NO 3
<211> LENGTH: 8
<212> TYPE: DNA
<213> ORGANISM: Human immunodeficiency virus
<220> FEATURE:
<221> NAME/KEY: misc_feature
<222> LOCATION: (3)..(3)
<223> OTHER INFORMATION: n is a, c, g, or t

<400> SEQUENCE: 3 ganatgga                                                                 8

<210> SEQ ID NO 4
<211> LENGTH: 11
<212> TYPE: DNA
<213> ORGANISM: Human immunodeficiency virus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 4
ganggnaana t                                                            11

<210> SEQ ID NO 5
<211> LENGTH: 20
<212> TYPE: DNA
<213> ORGANISM: Human immunodeficiency virus
<220> FEATURE:
<221> NAME/KEY: misc_feature
<222> LOCATION: (3)..(3)
<223> OTHER INFORMATION: n is a, c, g, or t

<400> SEQUENCE: 5
atngggcctg aaaatccata                                                   20
```

METHOD AND APPARATUS FOR ALIGNMENT OF DNA SEQUENCING DATA TRACES

This application is a continuation-in-part of U.S. patent application Ser. No. 09/628,736, filed Jul. 27, 2000 now U.S. Pat. No. 6,397,150.

BACKGROUND OF THE INVENTION

This application relates to a method for alignment of data traces obtained from a DNA sequencing apparatus, and to apparatus adapted for practicing of this method.

DNA sequencing is becoming an increasingly important diagnostic tool, and also forms an important component of research efforts such as the Human Genome Project. The most common sequencing procedures used today are based on the primer extension or "Sanger" methodology. In the "dye primer" version of Sanger DNA sequencing, a 5'-end-labelled oligodeoxynucleotide primer is bound sequence-specifically to a target DNA template which is to be sequenced. The primer is extended by a DNA polymerase enzyme, via incorporation of dNTPs. A chain-terminating dideoxy-NTP of one particular base type (A, C, G, T) is added to the reaction, to effect a termination of DNA chains at random positions along the sequence. The nested series of DNA fragments produced in this reaction is loaded on one lane of a thin denaturing polyacrylamide gel, and the bands are electrophoretically resolved, to produce a series of 5' end labeled bands in the profile of that lane. A set of four reactions (with chain termination occurring via ddA, ddC, ddG, ddT incorporation) is required for explicit determination of the positions of all four bases in the sequence, and typically is run on four adjacent lanes of a sequencing gel.

Data traces are collected indicating the peak positions in each of the four lanes of a gel. In an ideal system, these four data traces could simply be placed one over another and the sequence could be read. This reading process is called "base-calling." In practice, however, the data traces are not ideal because of a variety of factors including mobility differences between lanes and changes in resolution which occur as the size the fragments increases. Prior to the development of automated sequencing apparatus, the data traces were generally aligned by eye prior to base-calling, that is by a skilled technician looking at the traces and shifting the relative positions of the traces based on accumulated experience. One of the challenges of automated DNA sequencing is the proper alignment of the data traces using computer processing rather than human analysis.

Various approaches have been taken to the need for accurate trace alignment which is an essential prerequisite to accurate base-calling. One approach is the use of a multi-dye sequencer, in which the traces from all four bases are obtained from a single lane of a gel. (See, for example, U.S. Pat. Nos. 5,751,534 and 5,821,058.) This reduces many of the sources of variability, but requires the utilization of four different label types, and may involve an increase in the complexity of the detection apparatus. Another approach is described in commonly assigned U.S. Pat. No. 5,916,747. The present application provides yet another approach to the solution of this problem.

SUMMARY OF THE INVENTION

The present invention relies upon the conserved features of the sequence of the nucleic acid being sequenced to provide calibration markers for alignment of the data traces. Thus, in accordance with the invention, alignment of a plurality of data traces indicative of the positions of a plurality of nucleic acid base types in a target nucleic acid is achieved by selecting a set of three or more alignment points for each data trace. The alignment points are selected from among (1) a primer peak associated with unextended primer, (2) a full-length peak associated with full length product produced during a cyclic primer extension reaction or coupled amplification and sequencing reaction with one or two primers, and (3) internal peaks associated with internal bases that are highly conserved in the target nucleic acid. Each of the alignment points is associated with a reference position number reflecting the position of the alignment point with respect to the sequence as a whole. Sequencing position numbers are then assigned to each peak in each of the plurality of data traces in such a way as to maximize the number of times that the sequencing position number and the matching reference position number are assigned to a base of the same type. Finally, the data traces are aligned based on the assigned sequencing position numbers to provide aligned data traces for base-calling.

DETAILED DESCRIPTION OF THE INVENTION

Figure 1:
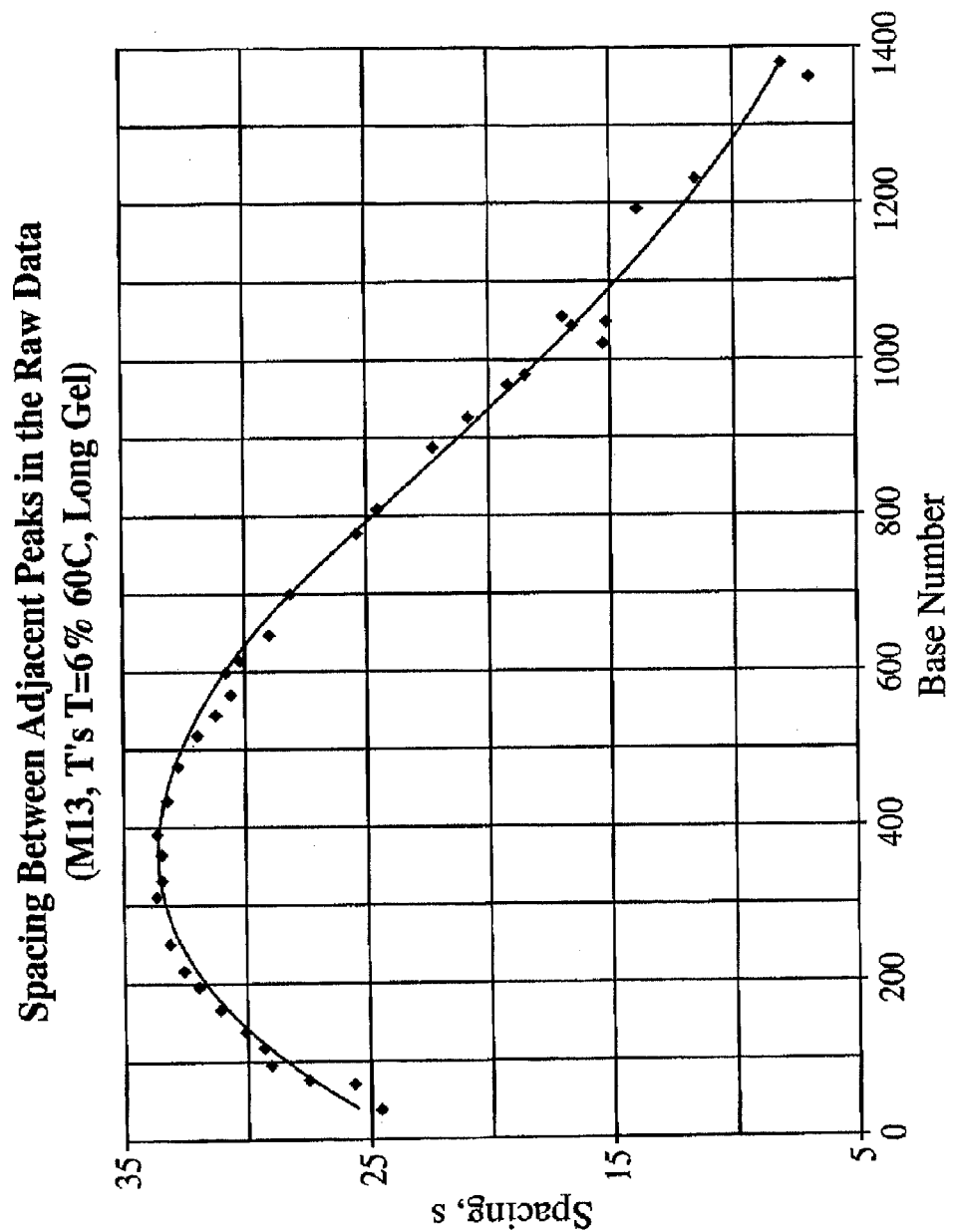
FIG. 1 is a plot of inter-peak spacing (units: sec) as a function of DNA chain length (base number), observed from raw data from a typical cycle-sequencing run on the Visible Genetics Long Read Tower™ sequencing apparatus (25 cm gel length).

This application relates to the alignment of DNA sequencing data traces of the type generated in a Sanger sequencing procedure. Each data trace reflects the positions of one type of nucleic acid base in a target nucleic acid sequence. In one embodiment of the invention, four data traces, one for each base type, are aligned using the method of the invention. This embodiment permits the explicit determination of all of the bases in the target nucleic acid. In some instances, however, it is not necessary to explicitly determine all the bases, for example when employing the methodology described in commonly assigned U.S. Pat. No. 5,834,189. Thus, in a more general sense, the invention relates to the alignment of a plurality (i.e., two or more) of data traces indicative of the positions of at least one nucleic acid base types in the target nucleic acid.

As used in the specification and claims of this application, the term alignment refers to the positioning of data traces relative to one another such that the peaks in the data traces are disposed in the correct order to provide a correct base-calling result, i.e., a result corresponding to the actual sequence of the target nucleic acid. Alignment can be done with different representations of the data traces, however. Thus, while alignment is perhaps easier to understand by consideration of graphical depictions of the data traces in which peaks representing each base are shown, other representations are useful. For example, the graphical data trace can be converted into a peak list (for example a listing of detection times after the start of electrophoresis). In the alignment procedure, each member of this peak list is associated with a unique sequencing position number indicating the position of the base represented by the peak within the sequence, and the peak lists are combined to place the peaks in order based on the sequencing position numbers.

As used in the specification and claims of this application, the term "highly conserved" refers to individual bases or combinations of bases in a target nucleic acid sequence which are of an expected type in a statistically high fraction of actual samples, for example, at least 90% of actual samples. Preferably, the highly conserved bases employed as internal alignment points are of an expected type in at least 98% of actual samples.

The method of the present invention makes use of the evolutionarily or biologically conserved aspects of the inherent sequence of the target nucleic acid to provide the basis for alignment of the data traces. The utilization of the inherent sequence for calibration can be applied to any target sequence for which there is a strong evolutionary or biological constraint on the range of variation which can reasonably be expected at certain positions. In accordance with the invention, the first step is the selection of alignment points used as reference points in the alignment of the traces. The alignment points are selected from among (1) the primer peak which is associated with unextended primer; (2) the full length peak associated with full length product produced during a cyclic primer extension reaction or coupled amplification and sequencing with one or two primers; and (3) internal peaks associated with internal bases that are highly conserved in the target sequence. Generally, a full length product peak is not produced when performing cycle sequencing from a circular template, and alternate alignment points can be used. The alignment points are each assigned a reference sequence number which is the known position of the alignment point relative to the target sequence as a whole. Sequencing position numbers are then assigned to the peaks in the data traces in such a way as to maximize the number of times that the sequencing position number and the matching reference position number are assigned to a base of the same type. In general, absent deviation in the sample from the expected base at a selected internal alignment point, all of the sequencing position numbers will be assigned to a base of the same type as the matching reference position number. The assigned sequencing position numbers are then used to align the data traces for base-calling.

When used, the primer peak and the full-length peak may be referred to collectively as "outer alignment points". The alignment points disposed at highly conserved bases within the target sequence are referred to collectively as "inner alignment points". The bases selected for use as inner alignment points may be individual bases. In a preferred embodiment of the invention, however, the inner alignment points are in fact heterogeneous multiplets of bases. Preferred multiplets are doublets or triplets. Multiplets of four bases or greater can be used, but may be rarely employed due to their relative infrequency of occurrence. As used herein, the term "heterogeneous multiplet" refers to a contiguous grouping of highly conserved bases which includes within the grouping at least two different types of bases. A heterogeneous multiplet counts as one inner alignment point for each data trace corresponding to a base within the multiplet.

The number of alignment points which are required to produce an accurate alignment of sequencing traces depends on a number of factors: the length (in bases) of the window over which the sequence is to be determined; how close to an acceptable alignment the lanes are to begin with; and whether any of the lanes display anomalously high or low electrophoretic mobility properties, which would require large mobility correction factors. A preferred number of alignment points is three for each data trace, for example two outer alignment points (which are the same for all data traces) and one inner alignment point (which is different for each data trace). An especially preferred number of alignment points is five for each data trace, for example, two outer alignment points (which are the same for all data traces) and three inner alignment points (which are different for each data trace).

In a well-behaved set of traces (which are relatively well aligned initially) this number of alignment points is sufficient for a sequence of in the order of 1000 nucleotides. In some circumstances, as few as three alignment points may be used. For example, if a region less than 200 nucleotides long is being sequenced, and if the four traces are relatively well aligned initially, and display no electrophoretic anomalies, then as few as two or three alignment points may suffice. The number of reference points depends, in general, on the nature of the misalignment. In the simplest case where two traces are shifted relative to each other, one parameter may suffice for alignment. In a more complex case, for example, where the trace is both shifted and stretched, the use of at least two reference points may be required. If the stretching is not linear, then the global alignment over the entire sequence may be more detailed to compensate for local misalignment.

In general, as the number of nucleotides in the data trace increases, the number of inner alignment points per data trace should also increase. Empirical data (see, e.g. example 4) indicates that for an average set of traces, one additional inner alignment point should be included for each additional 75-100 nt that is being analyzed.

The identification of inner alignment points depends on a knowledge of the expected sequence of the target nucleic acid. The following routine may be used, to obtain internal alignment points:
(1) identify the conserved regions (e.g. protein coding frames) within the genetic target;
(2) obtain an alignment of representative sequences; and
(3) step piecewise through the conserved region (for example, codon-by-codon through a protein coding sequence), and identify by means of a pattern-recognition process the most highly-conserved nucleotides.

This identification process can be aided, by reference to some database of "expert knowledge". For example, it is known from the field of molecular biology that, if a Met (methionine) residue is highly conserved within an amino-acid alignment, then "ATG" will almost certainly be the corresponding nucleotide triplet. (In the universal genetic code, there is only one codon—ATG—which specifies methionine.)

Once a set of possible inner alignment points is identified for a given target nucleic acid, the selection of the specific alignment points is not critical. It is, however, advantageous to utilize inner alignment points which are distributed at fairly even intervals over the length of the target sequence. Furthermore, there are certain additional criteria which are suitably applied depending on the type of inner alignment point being employed.

When using single conserved bases as the inner alignment points, it is desirable to avoid selection of inner alignment points from regions of sequence where the electrophoretic resolution R is low (R~1). This is because, in a region of low resolution, it will be very hard to detect the proper alignment points within a homopolymeric subsequence of bases. For example, consider positions 417-429 of the HIV-1 fragment produced in Example 1 below. The wild-type sequence is 5'-GAAAAAATAAAG-3' (SEQ ID NO: 1), and with >98% certainty, based on an alignment of HIV-1 sequences of different subtypes, positions 418, 420, 421, and 423 are expected to be "A". However, if the electrophoretic resolution happens to be low in this region, then it may be difficult to distinguish all the individual "A" residues within this subsequence.

This problem is largely avoided when heterogeneous multiplets are used as the inner alignment points since any given base in the multiplet necessarily has a near-neighbor base which is non-identical. Furthermore, the use of such heterogenous multiplets will allow a direct cross-alignment of different lanes at a single alignment point in a sequence determination. This provides an inherently greater certainty of alignment than does the less sophisticated strategy of defining totally distinct alignment points for the different lanes, i.e. using a T landmark as an alignment point for the T lane, and a C landmark as an alignment point for the C lane, and then adjusting the T and C alignment points for the correct distance apart.

The heterogenous doublet approach is general, and preferably includes for a complete implementation, only that the alignment window be large enough (approximately 200 nucleotides) that the following heterogenous doublets be found at least once:

| AC or CA, | AG or GA, | AT or TA |
| CG or GC, | CT or TC, | GT or TG |

A set of six doublets, as defined above, is sufficient to allow each lane to be aligned with every other lane, e.g. the A lane aligned with the C lane in the first (AC or CA) doublet, the C lane aligned with the G lane in the second (AG or GA) doublet, etc. This provides the greatest degree of certainty in cross-alignment of all the lanes. However, it is possible to align the four lanes using fewer doublets, but then the degree of certainty is correspondingly lower. Triplet inner alignment points may also be suitably employed. In particular, since the genetic code uses three bases to code for each amino acid, highly conserved amino acids from known protein structures can be used to direct the selection of highly conserved triplets of bases. In this case, the degree of cross-alignment achieved with a single alignment point may span two or three of the four data traces, such that as few as two triplets which between them include all four base types can provide a very good alignment check.

The above concept can be generalized. Long runs of heterogeneous bases, which are expected with high probability, can be used as "alignment locks" (alignment points of high certainty) within each examination window. In selecting the alignment points for use in aligning traces for a given sequence, the combination of alignment points may include inner and two outer alignment points, inner alignment points and one outer alignment point or it may include solely inner alignment points. When a cycle-sequencing or coupled amplification and sequencing process is employed such that the peaks for both outer alignment points are present, it is preferred to use both. Among the inner alignment points, some may be single bases, and some may derive from a heterogeneous multiplets, or all of the inner alignment points may be of the same type.

Once the alignment points have been selected, the next step is assignment of sequence position numbers to the peaks in the data traces. Various peak identification procedures are known in the art. The identification of peaks may take place using any appropriate procedure for this purpose.

When one or two outer alignment points are used, the first step is to identify the corresponding peaks(s) in the data traces and to assign to these peaks the sequence position number(s) equal to the reference position number(s) assigned to the outer alignment point(s). The region between the outer alignment points can then be visualized as being divided into alignment regions and intervening regions (see FIG. 3). The alignment regions correspond to the locations of the inner alignment peaks, with the intervening regions being the region of potential variability falling in between. The anticipated position of each alignment region is known and corresponds to the reference position number. The peaks appearing in these positions are therefore inspected and assigned sequence position numbers, to maximize the number of peaks where the base associated with a sequence position number is the same as the base known to be associated with the reference position number. Once the alignment is completed in the alignment region, the assignment of sequence position numbers in the intervening region is simplified, because the number of peaks that must fall between two defined end points is known, and the variability within the relatively short length of the intervening region is sufficiently low that it does not create difficulties. The length (in units of time) of the intervening region is divided by the anticipated number of intervening peaks (the difference between the two flanking reference position numbers) to arrive at an average peak spacing interval. Each data trace is then inspected for peaks occurring at this interval, and each peak is assigned an appropriate sequence position number.

The final step to produce aligned data traces is to combine the assigned position sequence numbers for each data trace into a concordance from which the overall sequence can be base-called. In the absence of ambiguities, this is a simple and straightforward combination process in which the sequence position numbers and their associated bases are listed in ascending numerical order. Ambiguities (such as two bases assigned the same position number) may be resolved by comparison to the sequence in the complementary strand, or flagged for attention by a human operator.

The method of the present invention is suitably practiced using an apparatus adapted for carrying out the analysis discussed above. Such an apparatus has the components shown in FIG. 10. As shown, the apparatus includes a DNA sequencer 101 comprising an electrophoresis system and a detection system for acquiring data traces reflecting the positions of nucleic acid bases in a target nucleic acid. DNA sequencers of this type are known in the art, including commercial sequencers manufactured by Visible Genetics Inc. and those described in U.S. Pat. Nos. 5,710,628 and 6,005,663 which are incorporated herein by reference. The acquired data trace is transmitted to a computer 102 for analysis. This transmission may be via a hard wired connection (as shown), or via a telecommunications link, wireless link, including radio and infra-red wireless links, by a manually transported storage medium (i.e., diskette or CD), or via any other means which results in the availability of the data traces to the computer 102 for analysis. The computer 102 has associated with it a storage device 103 in which inner alignment points and associated reference position numbers for one or more target nucleic acids are stored. The storage device may be local, i.e., a part of the computer 102, or remote, in which case it is accessible to the computer 102 through a network link. The computer includes a processor 104, which is programmed to receive the data traces, access the inner alignment points and associated reference position numbers, identify peaks in the data traces and assign sequence positions numbers to the identified peaks of the data traces which maximize the number of times that the sequencing position number and the matching reference position number are assigned to a base of the same type. The processor 104 then aligns the data traces based on the sequence position numbers for base-calling. Base-calling may occur in the same computer, or the aligned data traces may be output, for example on display 105. The type of computer and processor employed in the apparatus are not critical, provided they have sufficient capacity to carry out the programmed analysis. Specific examples of computer processors which can be used are PENTIUM and comparable processors now found in conventional personal computers, RISC processors and SPARC processors.

The invention will now be further explained with reference to non-limiting specific examples. In some of these examples, a portion of the sequence of the HIV-1 genome or the M13 genome is evaluated. It will be appreciated, however, that the present invention can be used in connection with sequence analysis of any target nucleic acid sequence which has conserved regions, and that HIV-1 and M13 are but non-limiting examples.

EXAMPLE 1

The number of internal alignment points which are required to produce an accurate alignment of sequencing traces will depend on (a) the length (in bases) of the window over which the sequence is to be determined, (b) the degree to which the traces are aligned initially, and (c) whether or not the individual lanes contain any electrophoretic anomalies that must be corrected. For an HIV-1 sequence of typical quality an ~1,100 nt "window" was used. The regularity of the electrophoretic properties of DNA bands in each lane was examined. If the electrophoretic mobility of a series of DNA fragments in a gel lane is a well-behaved function of chain length, then $t_N=t(N)$, the observed passage time ($t_N$) of a DNA chain as a function of chain length N, should be a continuous function with a continuous first derivative. Empirically, this function is highly regular. See, for example, the first derivative curve $dt_N/dN=f(N)$ for bands from an M13 sequencing ladder on the 27 cm MicroCel™ 700 electrophoresis gel (FIG. 1). This high degree of regularity implies that the $t_N=t(N)$ curve can be fit by a polynomial function. Alternatively, the {N, $t_N$} data set can be transformed to display a "corrected time scale" thus:

$$T_i = C^*(a_0 + a_1 t_i + a_2 t_i^2 + \ldots + a_n t_i^n)$$

where $T_i$=corrected time value, $t_i$=real time value, C is a scaling factor, and the coefficients {$a_0$, $a_1$, $a_2$, ..., $a_n$} are chosen so that $T_N=T(N)$ is now, as close as possible, a linear function of N.

Figure 2:
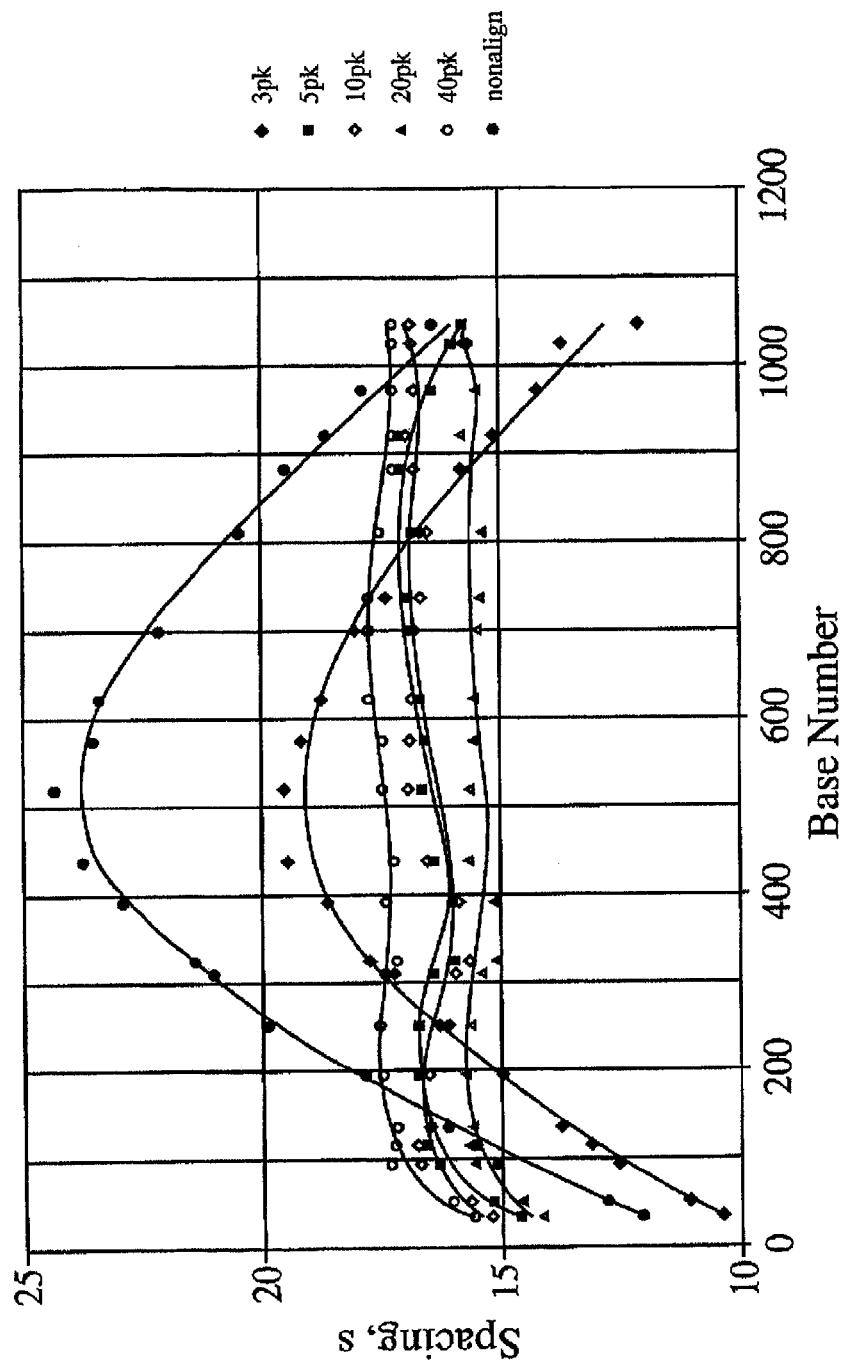
FIG. 2 is a plot of inter-peak spacing (units: sec) as a function of DNA chain length (base number), for aligned and "linearized" data. The raw data from FIG. 1 above were fit to a polynomial, and were then aligned and linearized by means of the transformation $t_i^* = C \cdot [a_0 + a_1 t_1 + a_2 t_i^2 + \ldots a_n t_i^n]$, where $t_i^*$=corrected time value; $t_i$=real time value; $a_0$, $a_1$, ..., $a_n$=fitted polynomial coefficients; and C=scaling factor. Different curves in this figure are drawn for different numbers of points (peaks) used for the linearization.
Figure 3:
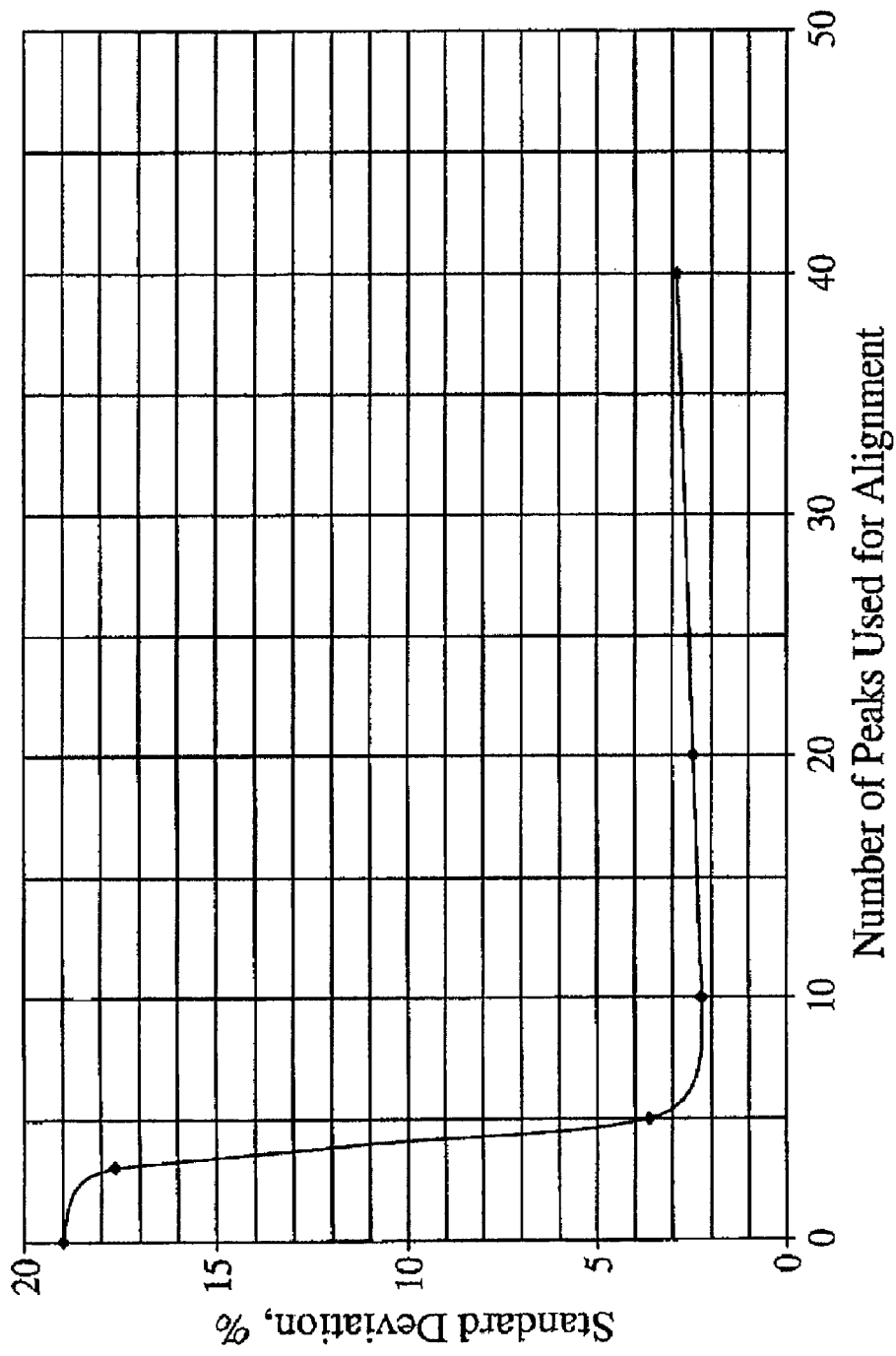
FIG. 3 is a plot of the percent standard deviation of peak spacing, as a function of the number of peaks used in the alignment.

The order of polynomial fitting that is required to allow the $t(N) \rightarrow T(N)$ transformation to produce an approximately linear output function was determined by testing polynomials of different degrees. FIG. 2 shows the results for no transformation, and for transformations based on 3 points ($2^{nd}$ order polynomial), 5 points ($4^{th}$ order polynomial), and 10, 20 or 40 points ($5^{th}$ order polynomial). FIG. 2 shows that a polynomial of order 4 is sufficient for linearization. FIG. 3 presents these data in another way, showing the deviation of points away from the best-fit line, as a function of the number of points used for the fitting routine. From this it follows that as few as three alignment points can be used to determine the correct alignment of sequencing data traces.

Figure 4:
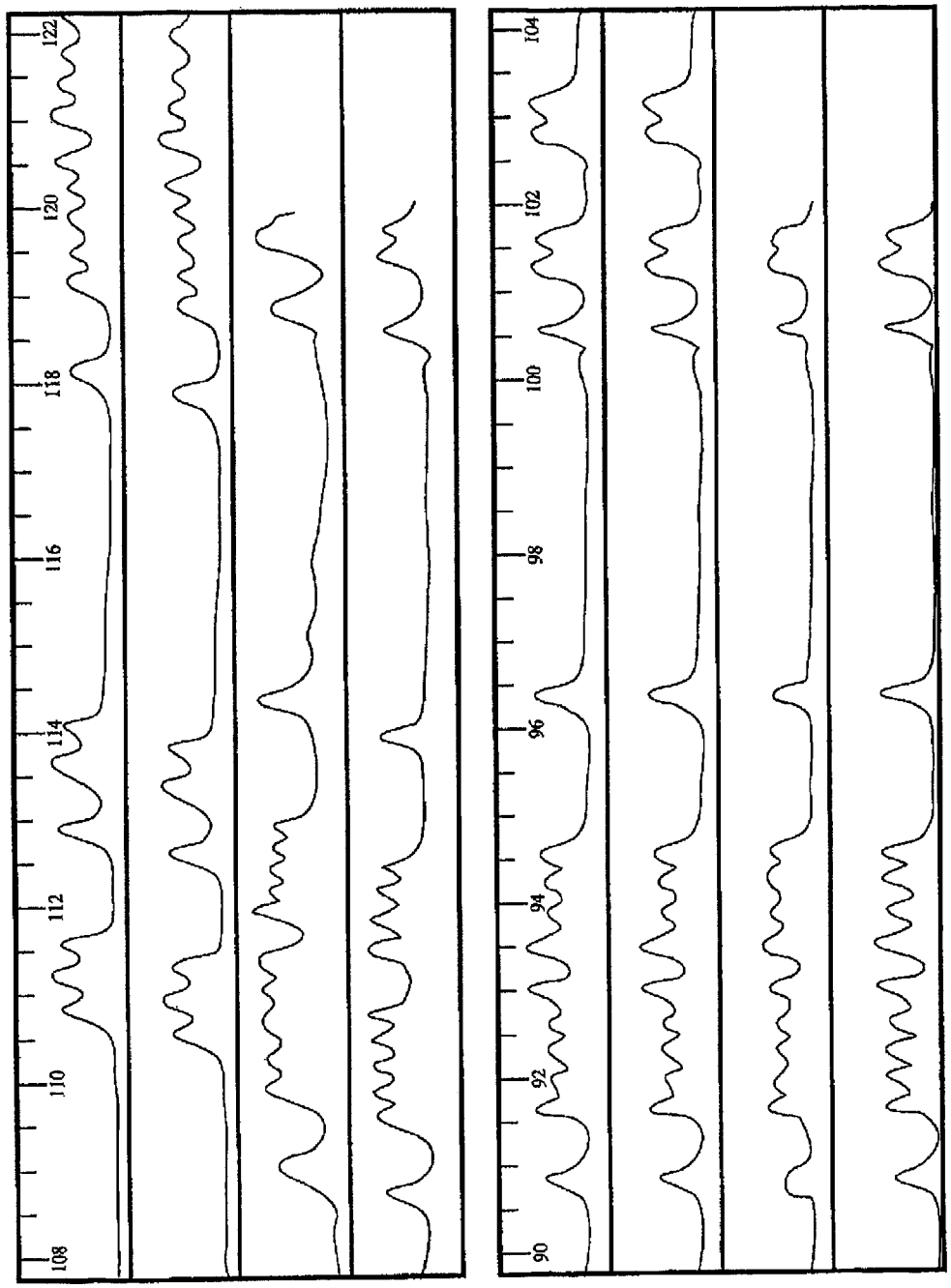
FIG. 4 is a plot of the 110-122 nt region of four sequence traces, presented either as raw unaligned traces (top), and as traces which have been aligned, by means of five points across entire gel run (bottom).
Figure 5:
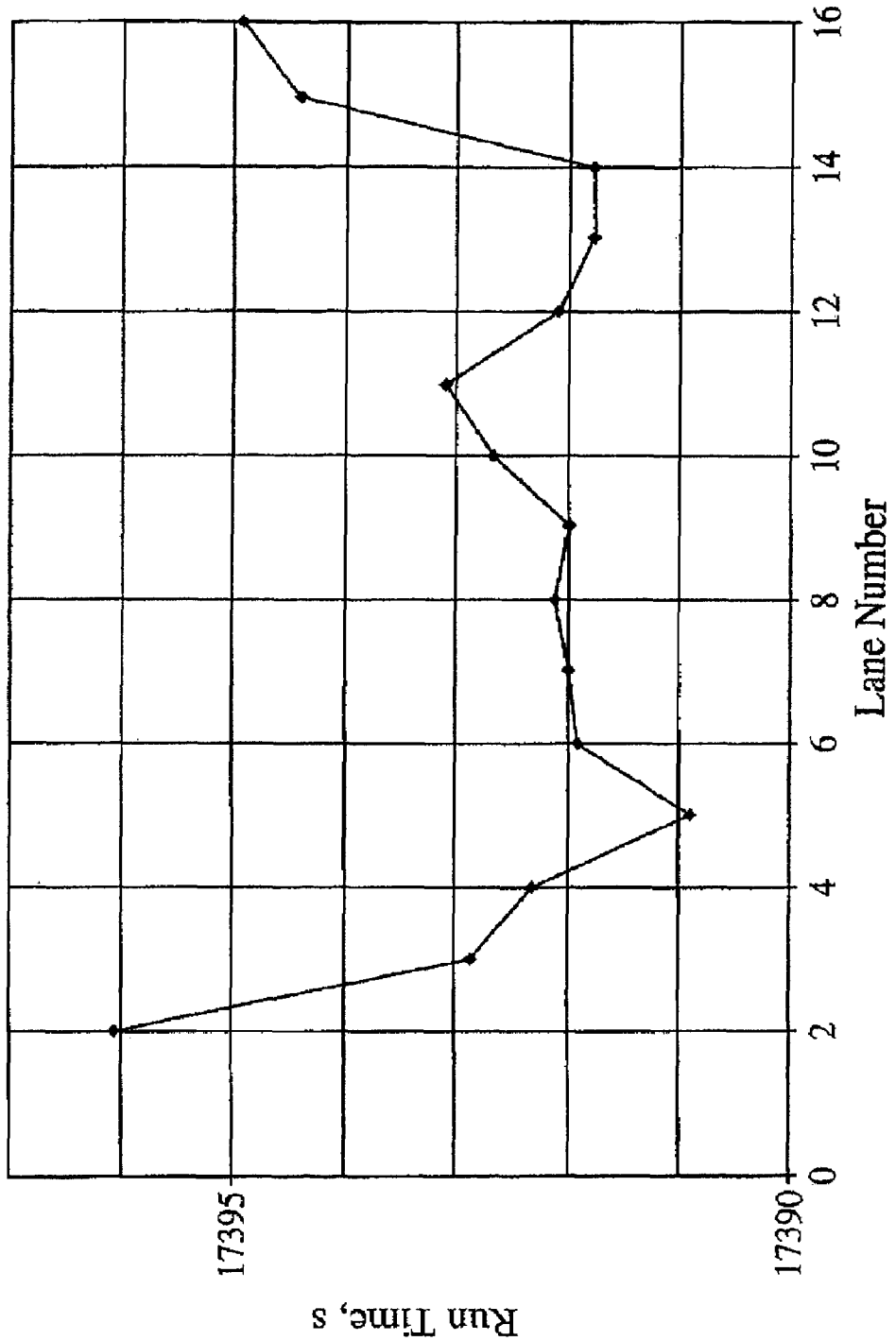
FIG. 5 is a plot of variation of the adjusted run time of band #1056, across lanes in a sequencing run on a Long Read Tower™ sequencing apparatus. There is less than ±2 seconds variation in the migration time of this band, across lanes. The average migration time is ~17,350 sec.

To test the conclusion that a small number of alignment points per data trace are in fact sufficient for achieving good alignment of four data traces, the four Cy5-labelled ladders from an M13 sequence determination were spiked with identical Cy5.5 calibration ladders using the Cy5.5 emissions from particular bands within these ladders for alignment purposes. FIG. 4A shows four adjacent traces before alignment, while FIG. 4B shows the same traces after alignment. Confirming the above results, it was found that as few as 5 bands, spaced 200 nt apart, were sufficient to allow alignment of traces with a high precision (±several parts per thousand in the time domain) (FIG. 5). The use of 10, 20, 30 or 40 bands did not confer any additional advantage for a sequence the size of the M13.

EXAMPLE 2

The alignment method of the present invention was applied to sequence determinations of an amplicon of HIV-1. Certain sequence positions within the flap region of the HIV-1 protease are found to be necessary to preserve a β-turn structure at the protein/solvent interface, which is critical for protease function. Site-directed saturation mutagenesis, combined with protease activity assays, have shown that I47, G49, I50, G51 and G52 (comprising the β-turn of the flap region) are extremely intolerant of substitutions, under the criterion that protease activity must be preserved (Shao W et al. (March 1997) Sequence requirements of the HIV-1 protease flap region determined by saturation mutagenesis and kinetic analysis of flap mutants. Proc. Nat. Acad. Sci. USA 94, 2243-2248.). Because protease activity is required for the HIV-1 virion to be viable, it follows that, in any isolate of live virus (e.g. from a patient plasma sample), codons for these amino acids (with very few possible substitutions) are expected at the appropriate positions in the genetic sequence. From this, it follows that such "pre-identified" nucleotides can be used as internal sequence calibrants, for trace-alignment.

Figure 6:
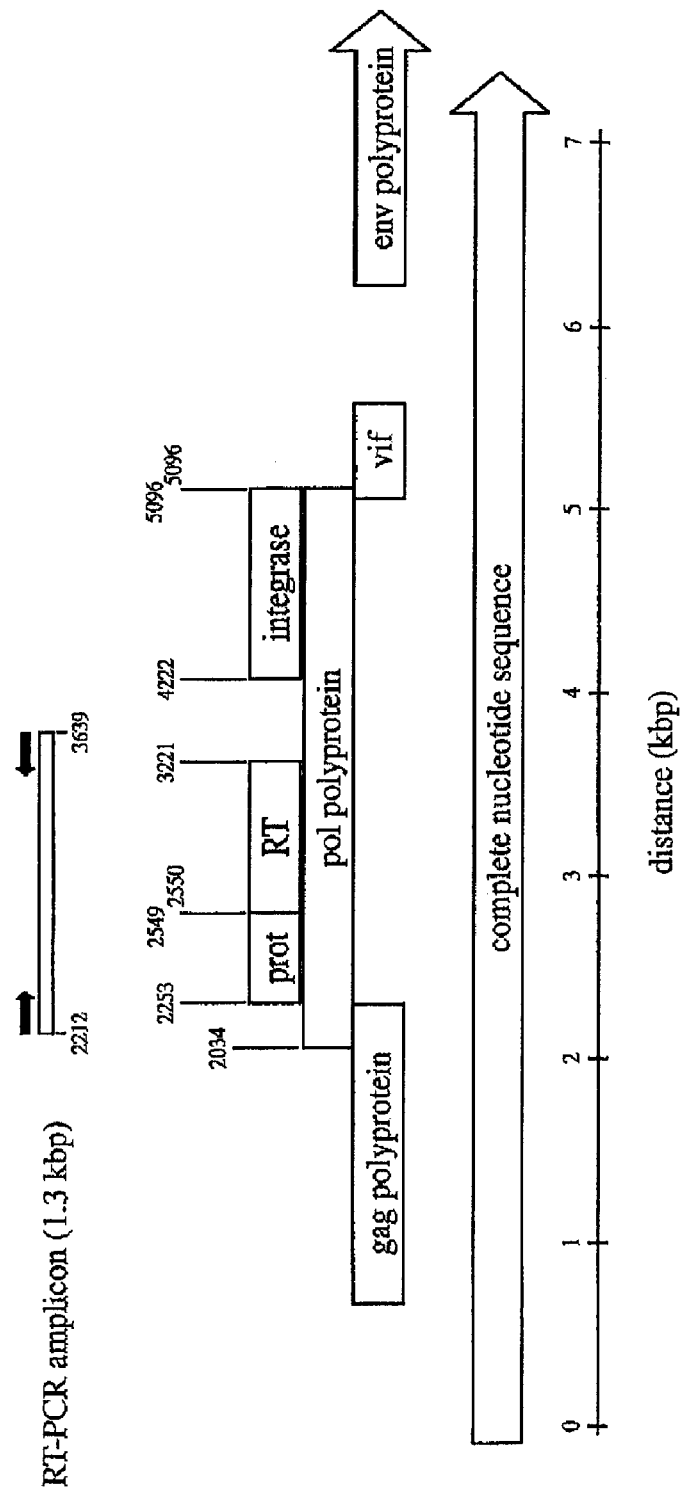
FIG. 6 is a schematic diagram of the genetic target used for testing the new trace-alignment method. The genetic target consists of the protease and reverse transcriptase coding sequences within HIV-1. A sequencing reaction was conducted on the RT-PCR amplicon, to produce an approximately 1100 bp product spanning the protease and RT coding sequences.

FIG. 6 is a schematic of a ~1.3 kb amplicon of HIV-1, the locations of the protease and RT coding sequences, and the locations of two primers chosen to allow a single CLIP sequencing reaction to read across the complete protease and reverse transcriptase coding sequences.

The goal was to be able to conduct an accurate sequence determination over a distance of ~1,100 bp, i.e., to generate sequencing fragments for the entire region of ~1,100 bp in a single reaction and to analyze these fragments in a single electrophoresis run.

When CLIP™ sequencing (as described in U.S. Pat. Nos. 5,789,168, and 5,830,657, incorporated herein by reference), is used with dye-labeled primers, then two absolute calibration points are provided automatically. These are (1) the dye-labeled primer peak; and (2) the full-length product peak (approximately 1100 nt long in the above example). When CLIP™ sequencing is used, the full-length peak is especially prominent, because it is generated first (before any sequencing ladders are produced). Because these two peaks define the endpoints of sequence produced by the assay, it is logical to choose them for calibration.

To obtain additional calibration points (besides the primer and full-length peaks), the sequence being amplified was examined to look for highly conserved positions. The a priori knowledge of HIV-1 sequence constraints was obtained from an alignment of 146 HIV-1 sequences of subtypes A, B, C, D, E, F, G, H, O (and including some sequences which could not clearly be assigned to one subtype or another). The samples from which the sequences were taken, in terms of HIV-1 subtypes, is given in the following Table.

TABLE 1

Subtype Composition of the HIV-1 alignment used to obtain calibration points.

| HIV-1 subtype | Number of sequences in alignment |
|---|---|
| A | 22 |
| B | 33 |
| C | 20 |
| D | 16 |
| E | 11 |
| F | 15 |
| G | 3 |
| H | 1 |
| unassigned | 12 |
| O | 13 |

From these sequences, a set of highly conserved bases (positions displaying ≧90% conservation in a multiple sequence alignment) which could potentially be used as inner alignment points was identified. Table 2 presents a set of probable alignment points, deduced over the 400-500 nt "window" of the HIV-1 sequence.

TABLE 2

Highly conserved alignment points over 400-500 nt sequencing window of HIV-1.

| Reference coordinates | Sequence coordinates | Amino acid | Most common Isotype (N/146) | Alternate Isotype (N/146; strain) |
|---|---|---|---|---|
| 2619, 20, 21 | 402, 03, 04 | Trp 24 | T G G (146) | none |
| 2622, 23, 24 | 405, 06, 07 | Pro 25 | C C - (145) | none |
| 2625, 26, 27 | 408, 09, 10 | Leu 26 | t T - (132) | C T - (14; o) |
| 2628, 29, 30 | 411, 12, 13 | Thr 27 | a C a (132) | T C T (13; o) |
| 2631, 32, 33 | 414, 15, 16 | Glu 28 | g a A (129) | A A A (11; c, o) A G A (04; o) |
| 2634, 35, 36 | 417, 18, 19 | Glu 29 | G A - (146) | none |
| 2637, 38, 39 | 420, 21, 22 | Lys 30 | A A - (146) | none |
| 2640, 41, 42 | 423, 24, 25 | Ile 31 | A T - (146) | none |
| 2646, 47, 48 | 429, 30, 31 | Ala 33 | G C - (145) | none |
| 2658, 59, 60 | 441, 42, 43 | Ile 37 | A T - (146) | none |
| 2661, 62, 63 | 444, 45, 46 | Cys 38 | T G - (146) | none |
| 2667, 68, 69 | 450, 51, 52 | Glu 40 | G A - (145) | none |
| 2669, 70, 71 | 453, 54, 55 | Met 41 | A T G (145) | none |
| 2672, 73, 74 | 456, 57, 58 | Glu 42 | G A - (146) | none |
| 2678, 79, 80 | 462, 63, 64 | Glu 44 | G A - (146) | none |
| 2681, 82, 83 | 465, 66, 67 | Gly 45 | G G - (146) | none |
| 2684, 85, 86 | 468, 69, 70 | Lys 46 | A A - (145) | none |
| 2687, 88, 89 | 471, 72, 73 | Ile 47 | A T - (145) | none |
| 2693, 94, 95 | 480, 81, 82 | Ile 50 | A T - (144) | none |
| 2696, 97, 98 | 483, 84, 85 | Gly 51 | G G g (130) | G G A (16; a, c, e, o) |
| 2699, 2700, 01 | 486, 87, 88 | Pro 52 | C C t (144) | none |
| 2702, 03, 04 | 489, 90, 91 | Glu 53 | G A a (141) | G A g (4; b, h, o, hiv) |
| 2705, 06, 07 | 492, 93, 94 | Asn 54 | A A T (132) | A A C (12; b, c, d, f) |
| 2708, 09, 10 | 495, 96, 97 | Pro 55 | C C A (132) | C C T (13; o) |
| 2711, 12, 13 | 498, 99, 500 | Tyr 56 | T A Y (146) | none |

The simplest way to use the above information is to make a list of potentially useful calibration bands for each track. Thus, over the 400-500 nt "window" of the HIV-1 sequence, the following bands are expected with very high (>98%) probability. (The probability is estimated from the sample of 146 HIV-1 sequences summarized in Table 1. If the estimated probability is less than 98%, then the estimate is noted in square brackets.)

TABLE 3

Reference singlets for strategy in which lanes are adjusted independently.

"A" track    411 [90%], 413 [91%], 415 [97%], 416, 418, 420, 421, 423,
(23 bands)   441, 451, 453, 457, 463, 468, 469, 471, 480, 490, 491 [97%],
             492, 493, 497 [91%], 499
"C" track    405, 406, 412, 430, 486, 487, 495, 496
(8 bands)
"G" track    403, 404, 414 [90%], 417, 429, 445, 450, 455, 456, 462, 465,
(16 bands)   466, 483, 484, 485 [90%], 489
"T" track    402, 408 [90%], 409, 424, 442, 444, 454, 472, 481, 488, 494,
(12 bands)   498

A more discriminating and robust approach is to employ "heterogeneous doublets" as calibration markers. These are defined as adjacent nucleotides in a sequence, which are highly conserved, and which are not the same base. Such doublets are very easy to detect, even when gel resolution R<1. For example, in the 400-500 nt "window" of the HIV-1 sequence, we expect to find 16 heterogeneous doublets with >98% probability, and an additional 6 heterogeneous doublets with >90% probability. These are indicated in Table 4 below.

TABLE 4

Reference doublets for a strategy in which lanes are cross-aligned.

| Doublet | Positions |
|---------|-----------|
| AC | 411-412 [90% of time] |
| AG | 416-4177 |
| AT | 423-424, 441-442, 453-454, 471-472, 480-481, 493-494 [90% of time] |
| CA | 412-413 [90% of time], 496-497 [90% of time] |
| GA | 414-415 [88% of time], 417-418, 450-451, 456-457, 462-463, 489-490 |
| TA | 498-499 |
| GC | 429-430 |
| TG | 402-403, 444-5, 454-455 |

There is an additional advantage in using the "heterogeneous doublet" approach. In theory, there are 12 possible such doublets (AC, AG, AT, CA, CG, CT, GA, GC, GT, TA, TC, TG). The use of such doublets allows a pairwise cross-alignment of different lanes in a sequence determination. This provides an inherently greater certainty of alignment, than does the "independent lane" strategy described above.

EXAMPLE 3

Figure 9A:
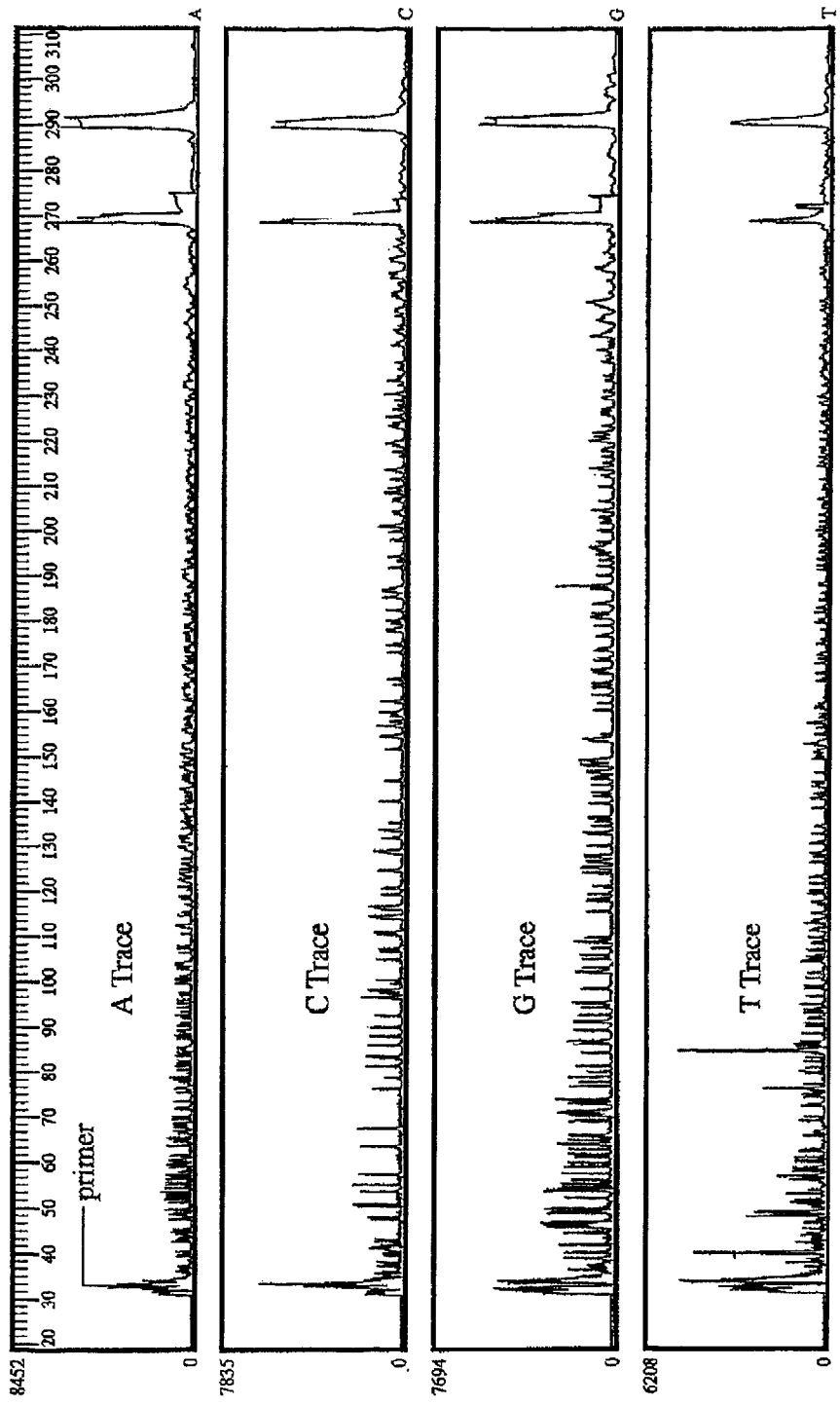
FIG. 9 is a diagram which illustrates the new alignment method. Panel A is a diagram showing two absolute alignment points, the primer and the full length CLIP product. Panel B is a diagram showing a "middle alignment region" over positions 417-430 of the HIV-1 region sequenced. There are three alignment doublets in this region: G417-A418, A423-T424, and G429-C430. Panel C is a diagram showing that the effect of the "middle alignment region" (pos. 417-430) is propagated over a ~75 nt wide window (pos 388-465).
Figure 9B:
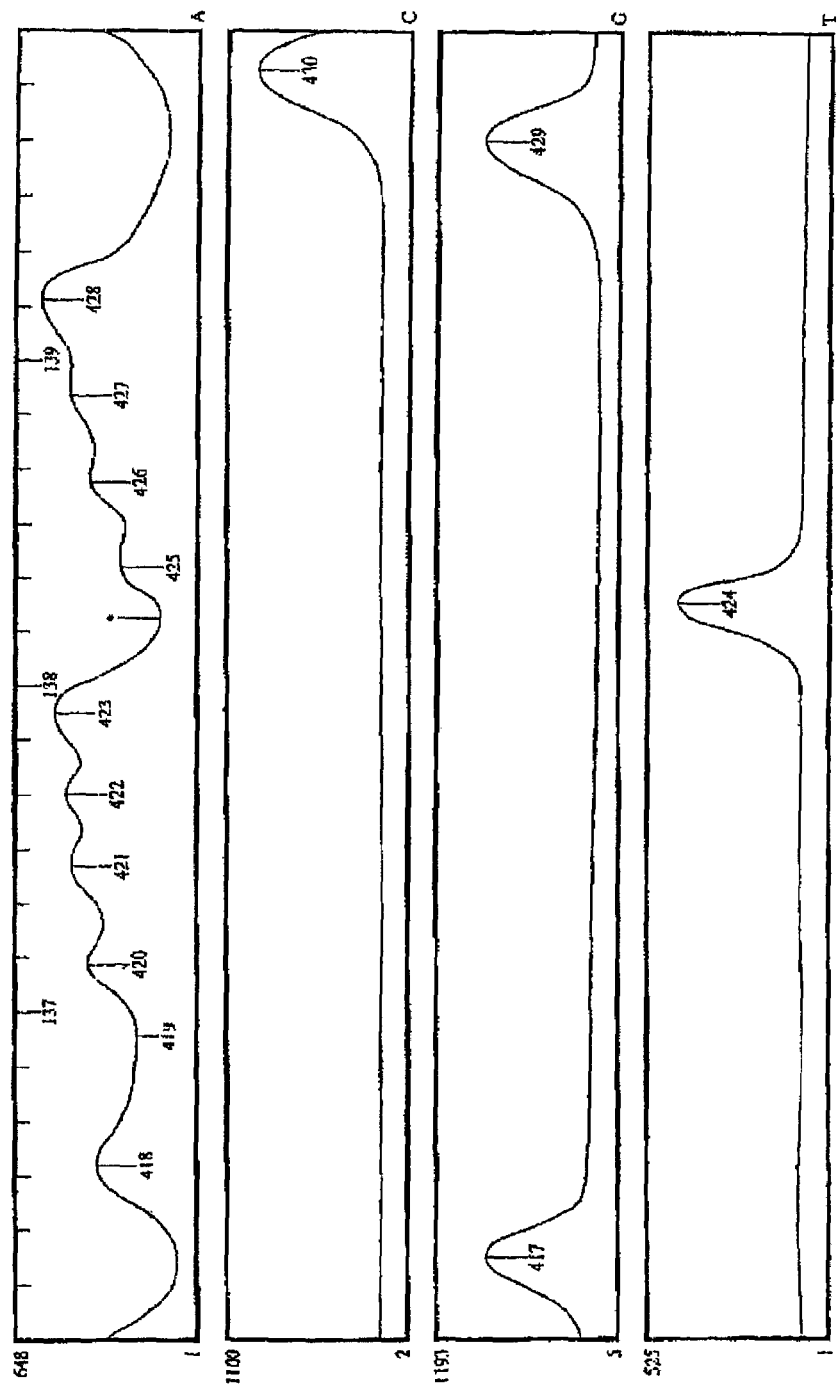

In order to align sequencing traces from the approximately 1100 nt HIV-1 sequence using two outer alignment points and one inner alignment point for base calling, the first step was a global alignment in which the four traces were aligned relative to the two outer alignment points (the primer peak and the full-length peak) (FIG. 9A). Next, a "middle alignment region" was chosen, and a set of three "heterogeneous doublets" were chosen on the basis of sequence conservation to define the first inner alignment point (FIG. 9B). In this example, the set of three heterogeneous doublets chosen all lie close together and together define a single inner alignment point which allows the four traces to be pairwise cross-aligned. The heterogeneous doublets are: the A423-C424 doublet (expected >98% of time), the G417-A418 doublet (expected >98% of time), and the G429-C430 doublet (expected >98% of time).

Figure 9C:
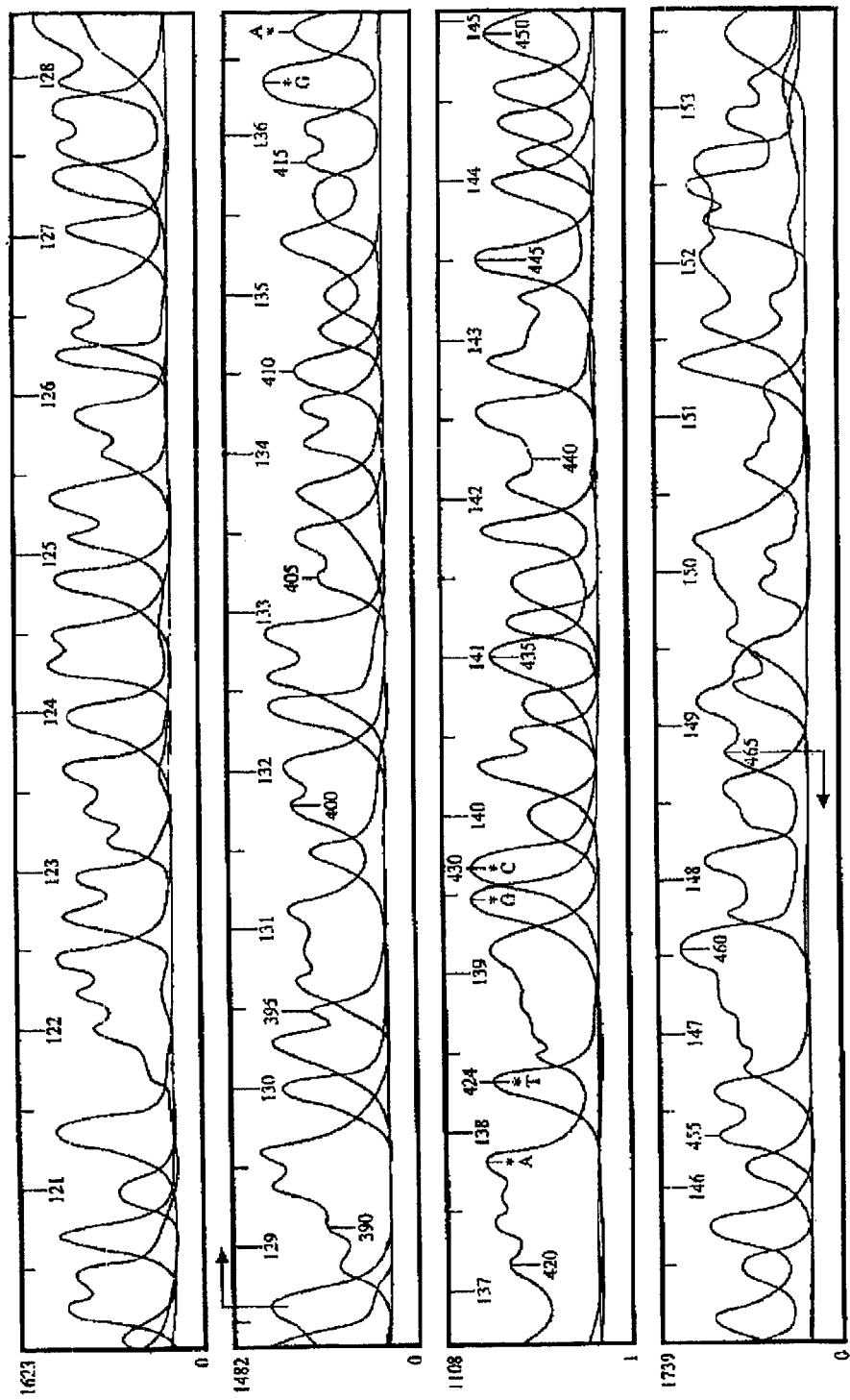

How far can such an alignment be extended, before another set of inner alignment points will be required? Upon analyzing the region around the A423-C424 doublet, a correct alignment of the four traces is produced between position C388 and G465, i.e. over a ~75 nt "window" (FIG. 9C). Outside of this window, especially at the high end, the traces become misaligned again. Thus, for this sequence window, it is preferable to employ a set of internal alignment points (e.g. "heterogenous doublets") at least every ~75 nt. For a sequence such as HIV-1 reverse transcriptase/protease, a sufficient number of "heterogeneous doublets" or "heterogeneous multiplets" exist to define a sufficient number of internal alignment points to allow successful alignment of all four traces.

EXAMPLE 4

Figure 7:
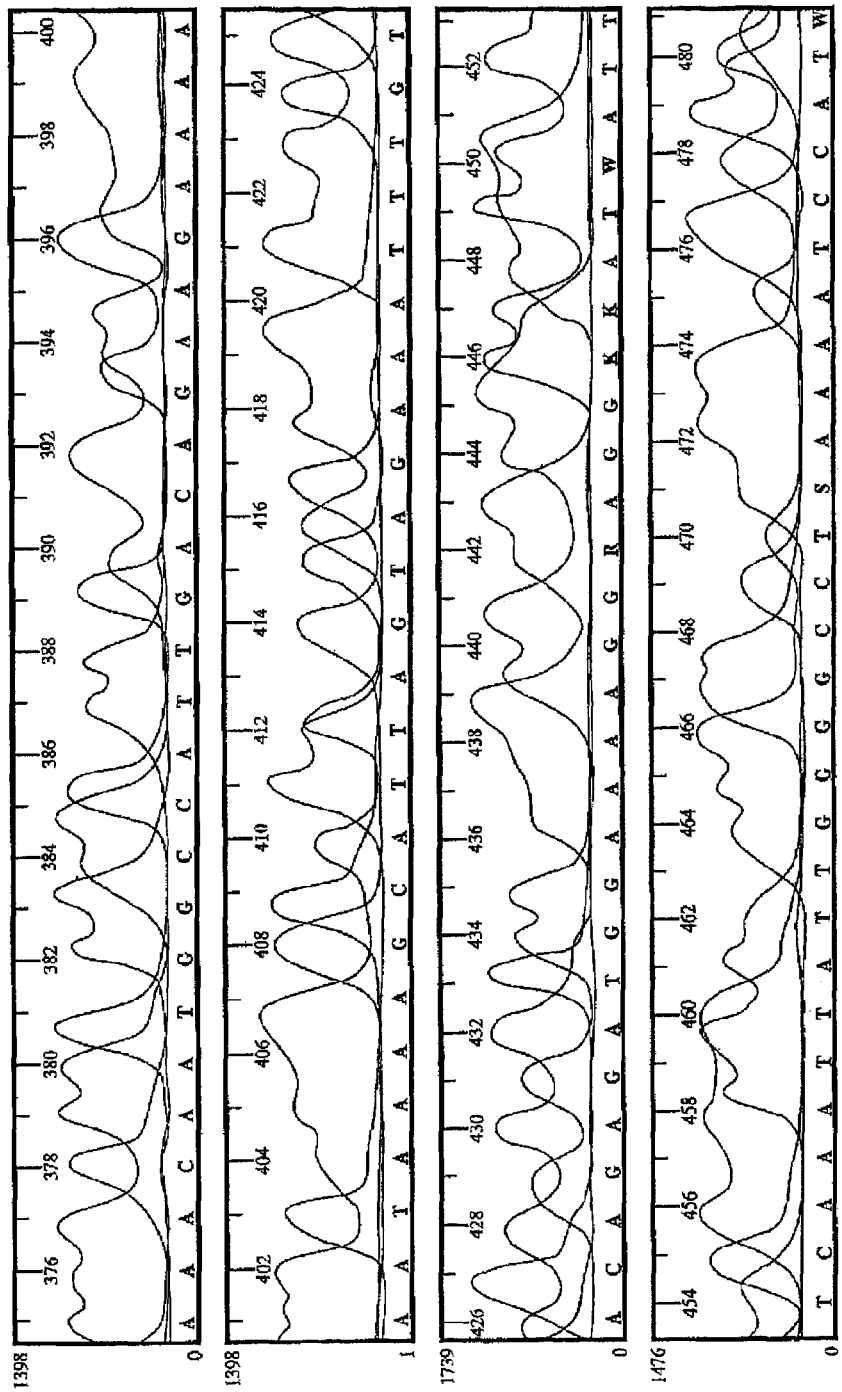
FIG. 7 is a typical GeneObjects™ 3.1 analysis, of a sequence window over approximate position 400-500. Alignment and base calling were done automatically.
Figure 8:
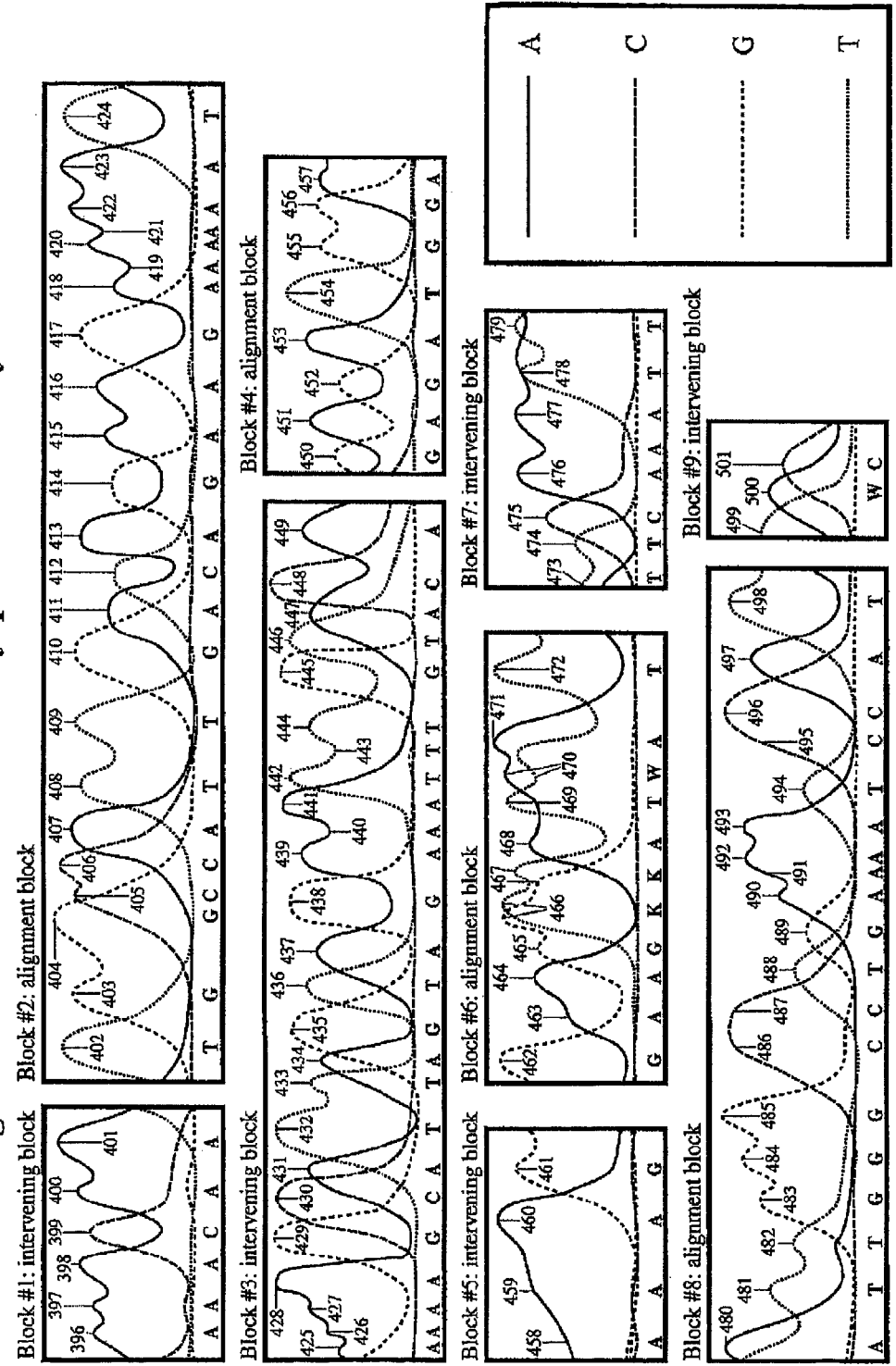
FIG. 8 is a schematic diagram illustrating how the 400-500 nt sequence region of the HIV-1 sequence test can be parsed into "alignment blocks" and "intervening blocks". The parsing operation was based on alignment of 146 HIV-1 sequences of subtypes A, B, C, D, E, F, G, H, and O.

FIGS. 7 and 8 illustrate alignment using longer multiplets. FIG. 7 shows a typical [automatic] GeneObjects analysis, in this case of an HIV-1 window over the 396-501 positions. The analysis was performed using the standard [automatic] method of trace-alignment, as implemented in GeneObjects version 3.01. The standard method of trace alignment in GeneObjects v. 3.01 has been described in PCT Application WO 98/00708, incorporated herein by reference, and involves the following steps: (1) selection of a first "alignment window" for all four lanes, for purpose of setting the "primary lock"; (2) aligning the four traces within the first window, by minimizing a cost function which describes the amount of overlap of peaks between the four traces; (3) moving to the next "alignment window" and repeating the process, until a piecewise alignment of the entirety of the four traces is achieved.

In the conventional alignment method (as embodied in GeneObjects v. 3.01), the first alignment window (which produces the "primary lock") must be without significant error. All subsequent alignment windows are predicated upon the primary lock that is produced from the first alignment window. Thus, one expects that, if each window is subject to a misalignment error, then these errors will add or compound, until eventually (after the Nth window) the alignment will be lost.

As an alternative, FIG. 8 illustrates how the new trace-alignment method would operate upon a set of data from a CLIP™ reaction. (1) Two outer alignment points would be provided by the primer and full-length peaks. These outer alignment points would determine the maximal amount of misalignment which possibly could occur. (2) Additional "internal" alignment points would then be assigned, preferably in approximate equidistant placement, in the sequence between the two outer alignment points.

The assignment of internal alignment points was performed by considering the 396-501 nt window, in the HIV-1 example. There are four highly significant sequence strings, as described in Table 5. According to the new method, the 396-501 nt window is parsed into 9 discrete sequence blocks, which alternate between two different types. The first type of sequence block (an "alignment block") contains sequence which we have a high probability of knowing a priori (blocks # 2, 4, 6, 8). The second type of sequence block (an "intervening block") contains sequence for which our pre-existing knowledge is much less certain (blocks # 1, 3, 5, 7, 9). Essential conserved amino acids will map to within the "alignment blocks", while mutational hotspots will map to within the "intervening blocks".

TABLE 5

Reference Multiplets for Strategy Which Involves Cross-Lane Alignments.

| Position | Length | Sequence | Probability ratio* |
|---|---|---|---|
| 402-424 | 23 | TGG CCN TTN ACA GAA GAA AAN AT (SEQ ID NO:2) | $4^{40} \square 10^{12}$ |
| 450-457 | 8 | GAN ATG GA (SEQ ID NO:3) | $4^{7} \square 16{,}000$ |
| 462-472 | 11 | GAN GGN AAN AT (SEQ ID NO:4) | $4^{8} \square 65{,}000$ |
| 480-499 | 20 | ATN GGG CCT GAA AAT CCA TA (SEQ ID NO:5) | $4^{19} \square 3 \cdot 10^{11}$ |

*ratio of probabilities of finding the specified sequence, based on either (1) an alignment of N = 146 sequences of all major HIV-1 subtypes as described in Table 2, or (2) a completely random occurrence, computed by means of Kolmogorov probability model (see Feller, W. (1968) An Introduction to Probability Theory and its Applications. Volume I, 3rd Edition. J. Wiley & Sons, New York.).

This example highlights a significant advantage of the present method. There is an aberrant feature of block #6 in FIG. 8. This block is an "alignment block", which implies an a priori knowledge of its sequence with a high degree of certainty. However, GeneObjects v. 3.1 has erroneously analyzed this block, causing the T-track between positions 466-470 to be shifted too far to the right by about ⅓ of a nucleotide position. In turn, a base-insertion has erroneously been called between positions 465 and 466 (as indicated by a solid box in FIG. 8). This insertion does not make biological sense. It would cause a +1 frameshift, leading to the production of non-functional reverse transcriptase. Consequently, the HIV-1 virus would be non-viable, and therefore would not exist in a patient's plasma sample. This type of insertion error (within an "alignment block" that codes for an essential part of an essential protein) is avoided by the trace-alignment method of the present invention, which would force the positioning of the alignment block at the correct location.

EXAMPLE 5

Figure 10:
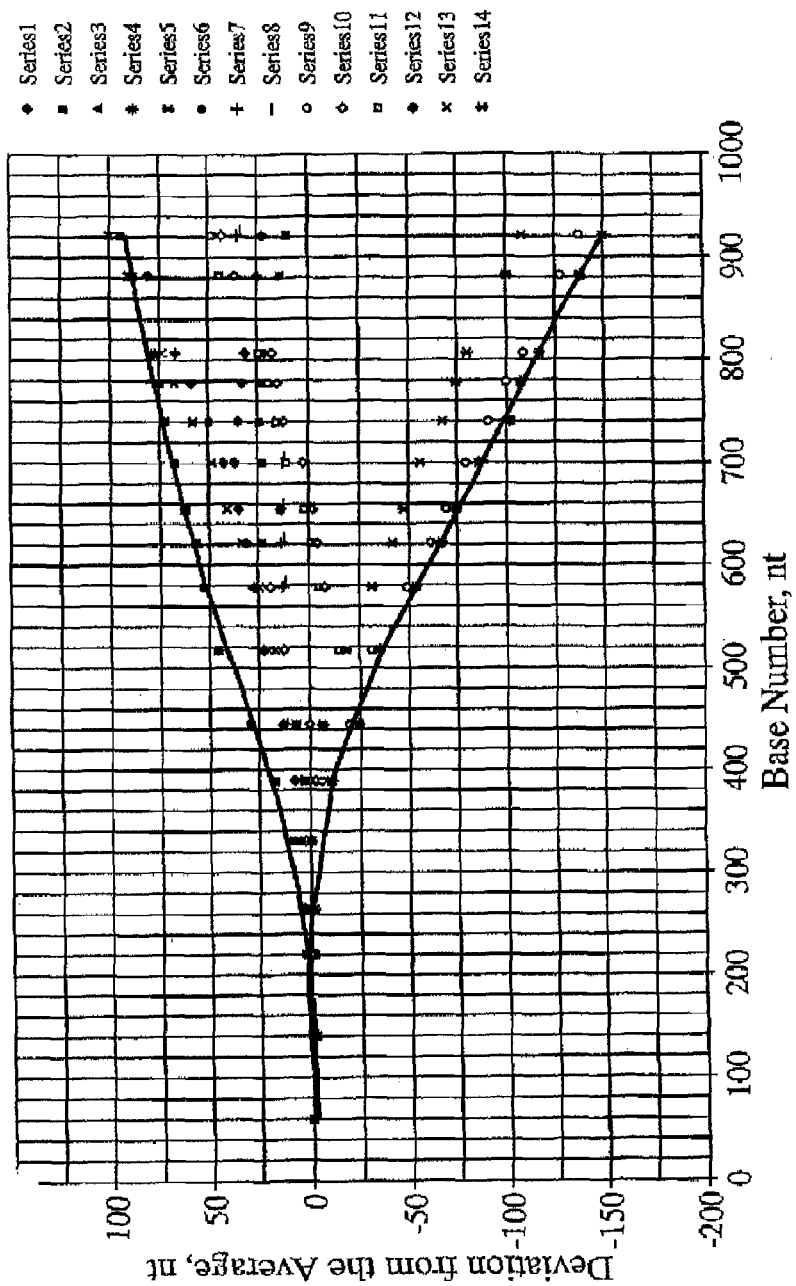
FIG. 10 shows the deviation of the peak position with the given base number in each trace from the average for this peak, in an analysis of M13 sequence.
Figure 11:
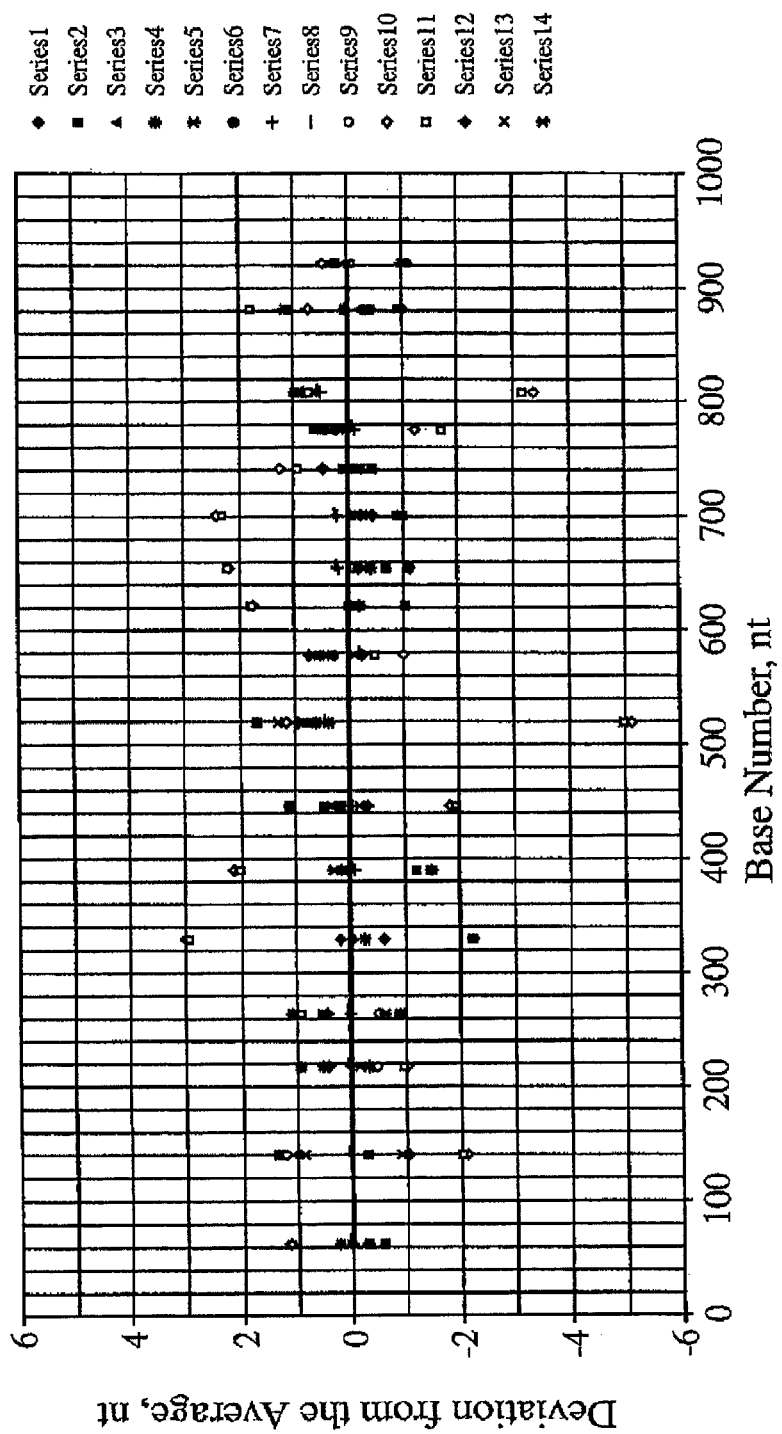
FIG. 11 shows aligned M13 sequence data of FIG. 10 based on seventeen internal reference points selected in the range of 60-922 nucleotides.
Figure 12:
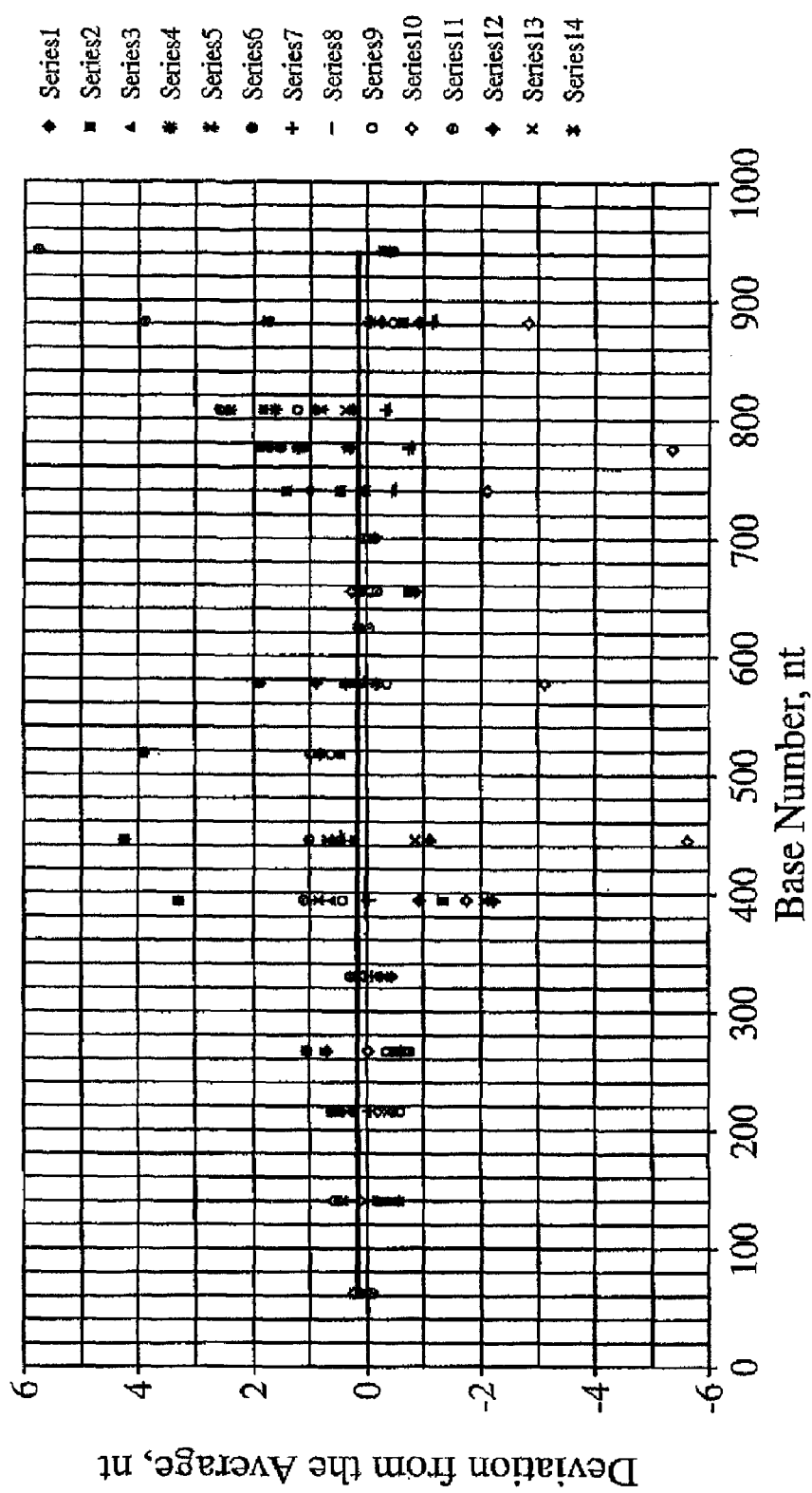
FIG. 12 shows aligned M13 sequence data of FIG. 10 based on six internal reference points.

Approximately 950 nt of M13 was sequenced with Cy5.5 labelled ladders, and run in 14 lanes of a Microcel™ 700 electrophoresis gel with 5.5% acrylamide. The deviation of peak position (of the unaligned data traces) is shown in FIG. 10. As can be seen, in the early portions of the sequencing run, within the first 300 nt, the position of the peak with the same base number stays approximately the same for all the gel lanes. As the length of the run increases, corresponding to the length of the fragment being sequenced, the variability of the position becomes increasingly high. This difference reaches up to 100-150 bases at the 800-900 nt region. The data of FIG. 10 are aligned in FIG. 11. Alignment was based on the internal reference points selected in the range of 60-922 nt. 17 reference peaks, approximately evenly distributed along the trace were selected for alignment. FIG. 11 shows that the alignment of the present invention compensates for the deviation, even in the 800-900 nt region, with residual deviation from the average not exceeding +/−5 nt. Further alignment of the FIG. 10 data is shown in FIG. 12, with alignment being based on the use of six internal reference points. Once again, the alignment of the present invention compensates for the deviation shown in FIG. 10, resulting in a small deviation from the average, less than +/−6 nt.

---

What is claimed is:

1. A method for alignment of a plurality of data traces indicative of the positions of a plurality of nucleic acid base types in a target nucleic acid sequence, comprising the steps of:

(a) selecting for each data trace one or more alignment points corresponding to an internal peak associated with internal bases that are highly conserved in the target nucleic acid, wherein said highly conserved internal bases are of expected type in at least 98 percent of actual samples, and further selecting alignment points selected from the group consisting of a primer peak associated with unextended primer, a full-length peak associated with full length product produced during a cyclic primer extension reaction with two primers, and assigning to each selected alignment point a reference position number reflecting the relative position of the alignment point with respect to the sequence as a whole;

(b) assigning a sequence position number to each peak in each of the plurality of data traces that maximizes the number of times that the sequence position number and the reference position number are assigned to a base of the same type;

(c) aligning the data traces based on the assigned sequence position numbers;

(d) determining the sequence of the nucleic acid bases according to the aligned data traces; and (e) displaying the determined sequence of nucleic acid bases.

2. The method of claim 1, wherein at least some of the internal peak alignment points are members of heterogeneous multiplets.

3. The method of claim 1, wherein all of the internal peak alignment points are members of heterogeneous multiplets.

4. The method of claim 1, wherein four data traces, one for each nucleotide base type, are aligned.

5. A method for alignment of a plurality of data traces indicative of the positions of a plurality of nucleic acid base types in a target nucleic acid sequence, comprising the steps of:

(a) selecting for each data trace a set of three or more alignment points, wherein at least one alignment point corresponds to an internal peak associated with internal bases that are highly conserved in the target nucleic acid, wherein said highly conserved internal bases are of expected type in at least 98 percent of actual samples, and further selecting alignment points selected from the group consisting of a primer peak associated with unextended primer, a full-length peak associated with full length product produced during a cyclic primer extension reaction with two primers, and assigning to each selected alignment point a reference position number reflecting the relative position of the alignment point with respect to the sequence as a whole;

(b) determining the average peak spacing interval between each of the alignment points in each of the plurality of data traces and assigning sequence position numbers to peaks occurring at each interval that maximizes the number of times that the sequence position number and the reference position number are assigned to a base of the same type, wherein the sequence position numbers are used for aligning the data traces based on the assigned sequence position numbers;

(c) aligning the data traces based on the assigned sequence position numbers;

(d) determining the sequence of the nucleic acid bases according to the aligned data traces; and (e) displaying the determined sequence of nucleic acid bases.

6. A method for alignment of a plurality of data traces indicative of the positions of a plurality of nucleic acid base types in a target nucleic acid sequence, comprising the steps of:

(a) selecting for each data trace a set of five or more alignment points, wherein at least one alignment point corresponds to an internal peak associated with internal bases that are highly conserved in the target nucleic acid, wherein said highly conserved internal bases are of expected type in at least 98 percent of actual samples, and further selecting alignment points selected from the group consisting of a primer peak associated with unextended primer, a full-length peak associated with full length product produced during a cyclic primer extension reaction with two primers, and assigning to each selected alignment point a reference position number reflecting the relative position of the alignment point with respect to the sequence as a whole;

(b) determining the average peak spacing interval between each of the alignment points in each of the plurality of data traces and assigning sequence position numbers to peaks occurring at each interval that maximizes the number of times that the sequence position number and the reference position number are assigned to a base of the same type, wherein the sequence position numbers are used for aligning the data traces based on the assigned sequence position numbers;

(c) aligning the data traces based on the assigned sequence position numbers;

(d) determining the sequence of the nucleic acid bases according to the aligned data traces; and (e) displaying the determined sequence of nucleic acid bases.

7. The method of claim 1, further comprising the steps of determining the average peak spacing interval between each of the alignment points and assigning a sequence position number to peaks occurring at each interval, wherein the sequence position numbers are used for aligning the data traces based on the assigned sequence position numbers.

8. The method of claim 5, wherein at least some of the internal peak alignment points are members of heterogeneous multiplets.

9. The method of claim 5, wherein all of the internal peak alignment points are members of heterogeneous multiplets.

10. The method of claim 5, wherein four data traces, one for each nucleotide base type, are aligned.

11. The method of claim 6, wherein at least some of the internal peak alignment points are members of heterogeneous multiplets.

12. The method of claim 6, wherein all of the internal peak alignment points are members of heterogeneous multiplets.

13. The method of claim 6, wherein four data traces, one for each nucleotide base type, are aligned.

* * * * *